(12) United States Patent
James

(10) Patent No.: US 11,998,287 B1
(45) Date of Patent: Jun. 4, 2024

(54) PLATFORM FOR FACILITATING REMOTE ROBOTIC MEDICAL PROCEDURES

(71) Applicant: DOPL TECHNOLOGIES INC., Bothell, WA (US)

(72) Inventor: Ryan Christopher James, Bothell, WA (US)

(73) Assignee: DOPL TECHNOLOGIES INC., Bothell, WA (US)

(*) Notice: Subject to any disclaimer, the term of this patent is extended or adjusted under 35 U.S.C. 154(b) by 1024 days.

(21) Appl. No.: 16/823,234

(22) Filed: Mar. 18, 2020

Related U.S. Application Data

(60) Provisional application No. 62/991,010, filed on Mar. 17, 2020, provisional application No. 62/932,018, (Continued)

(51) Int. Cl.
*A61B 34/30* (2016.01)
*A61B 17/00* (2006.01)
(Continued)

(52) U.S. Cl.
CPC .......... *A61B 34/30* (2016.02); *A61B 18/1492* (2013.01); *B25J 9/0009* (2013.01); *B25J 9/1689* (2013.01); *B25J 9/1694* (2013.01); *B25J 9/1697* (2013.01); *B25J 19/02* (2013.01); *G06F 16/24568* (2019.01); *G06F 16/254* (2019.01); *H04L 67/12* (2013.01); (Continued)

(58) Field of Classification Search
CPC ................ A61B 34/30; A61B 18/1492; A61B 2017/00022; A61B 2017/00199; A61B 2017/00212; A61B 2017/00221; A61B 2018/00345; A61B 2018/00577; A61B 2034/301; B25J 9/0009; B25J 9/1689; B25J 9/1694; B25J 9/1697; B25J 19/02; G06F 16/24568; G06F 16/254; H04L 67/12; G05B 2219/40153
See application file for complete search history.

(56) References Cited

U.S. PATENT DOCUMENTS 5,391,199 A 2/1995 Ben-Haim
5,640,967 A 6/1997 Fine et al.
(Continued)

*Primary Examiner* — Faisal M Zaman
(74) *Attorney, Agent, or Firm* — Leonid Kisselev

(57) ABSTRACT

A hardware platform includes adapters to interface with medical provisioning equipment involved in a remote robotic medical procedure at a patient site and a software system component, potentially cloud-based, to process real-time incoming data streams and a database to store the data streams for later use or archival. Each data stream can itself contain different types of sensory data. The software system component provides overall control and overrideable supervision over the remote robotic operations includes a state manager that synergistically processes the incoming data streams possibly of varying transmission rates, times of receipt or transmission, resolution, and quality. The state manager forms a near- or real-time virtual representation of the operative field. The software system component includes a data broker that can parse the RTVR into subsets data tailored to the needs of the medical provisioning and monitoring equipment, which may also be deployed and co-located at the patient site.

19 Claims, 6 Drawing Sheets

Related U.S. Application Data filed on Nov. 7, 2019, provisional application No. 62/819,716, filed on Mar. 18, 2019.

(51) Int. Cl.

| | |
|---|---|
| *A61B 18/00* | (2006.01) |
| *A61B 18/14* | (2006.01) |
| *B25J 9/00* | (2006.01) |
| *B25J 9/16* | (2006.01) |
| *B25J 19/02* | (2006.01) |
| *G06F 16/2455* | (2019.01) |
| *G06F 16/25* | (2019.01) |
| *H04L 67/12* | (2022.01) |

(52) U.S. Cl.
CPC ............... *A61B 2017/00022* (2013.01); *A61B 2017/00199* (2013.01); *A61B 2017/00212* (2013.01); *A61B 2017/00221* (2013.01); *A61B 2018/00345* (2013.01); *A61B 2018/00577* (2013.01); *A61B 2034/301* (2016.02); *G05B 2219/40153* (2013.01)

(56) References Cited

U.S. PATENT DOCUMENTS

| | | | |
|---|---|---|---|
| 5,697,377 A | 12/1997 | Wittkampf | |
| 6,226,547 B1 | 5/2001 | Lockhart et al. | |
| 6,381,485 B1 | 4/2002 | Hunter et al. | |
| 6,650,927 B1 | 11/2003 | Keidar | |
| 6,659,939 B2 * | 12/2003 | Moll ...................... | A61B 34/30 600/102 |
| 7,263,397 B2 | 8/2007 | Hauck et al. | |
| 7,543,239 B2 | 6/2009 | Viswanathan et al. | |
| 7,630,752 B2 | 12/2009 | Viswanathan | |
| 7,711,847 B2 | 5/2010 | Dhupelia et al. | |
| 7,961,926 B2 | 6/2011 | Viswanathan | |
| 8,024,024 B2 | 9/2011 | Viswanathan et al. | |
| 8,202,244 B2 | 6/2012 | Cohen et al. | |
| 8,398,541 B2 | 3/2013 | DiMaio et al. | |
| 8,467,860 B2 | 6/2013 | Salazar et al. | |
| 8,694,157 B2 | 4/2014 | Wenderow et al. | |
| 8,725,801 B2 | 5/2014 | Kariathungal et al. | |
| 8,790,297 B2 | 7/2014 | Bromander et al. | |
| 8,825,144 B2 | 9/2014 | Starks | |
| 9,095,681 B2 | 8/2015 | Wenderow et al. | |
| 9,111,016 B2 | 8/2015 | Besson et al. | |
| 9,148,443 B2 | 9/2015 | Chizeck et al. | |
| 9,211,160 B2 | 12/2015 | Pivotto et al. | |
| 9,220,568 B2 | 12/2015 | Bromander et al. | |
| 9,345,498 B2 | 5/2016 | Creighton | |
| 9,471,268 B2 | 10/2016 | Li | |
| 9,533,121 B2 | 1/2017 | Pacheco et al. | |
| 9,545,497 B2 | 1/2017 | Wenderow et al. | |
| 9,690,374 B2 | 6/2017 | Clement et al. | |
| 9,691,173 B2 | 6/2017 | Gay et al. | |
| 9,691,175 B2 | 6/2017 | Rane | |
| 9,700,698 B2 | 7/2017 | Pacheco et al. | |
| 9,724,493 B2 | 8/2017 | Pacheco et al. | |
| 9,741,169 B1 | 8/2017 | Holz | |
| 9,746,686 B2 | 8/2017 | Haddick | |
| 9,750,577 B2 | 9/2017 | Pacheco et al. | |
| 9,795,764 B2 | 10/2017 | Pacheco et al. | |
| 9,833,293 B2 | 12/2017 | Wenderow et al. | |
| 9,883,878 B2 | 2/2018 | Creighton et al. | |
| 9,888,973 B2 | 2/2018 | Olson et al. | |
| 9,962,229 B2 | 5/2018 | Blacker et al. | |
| 9,993,614 B2 | 6/2018 | Pacheco et al. | |
| 9,999,751 B2 | 6/2018 | Pacheco et al. | |
| 10,258,285 B2 | 4/2019 | Hauck et al. | |
| 10,332,628 B2 | 6/2019 | Chkoundali et al. | |
| 10,751,546 B2 * | 8/2020 | Takayanagi .......... | A61N 5/1031 |
| 2003/0216664 A1 | 11/2003 | Suarez | |
| 2004/0087877 A1 | 5/2004 | Besz et al. | |
| 2007/0040670 A1 | 2/2007 | Viswanathan | |
| 2007/0060916 A1 | 3/2007 | Pappone | |
| 2007/0066911 A1 | 3/2007 | Klingenbeck-Regn | |
| 2008/0015427 A1 | 1/2008 | Kastelein et al. | |
| 2008/0059598 A1 | 3/2008 | Garibaldi et al. | |
| 2008/0183190 A1 * | 7/2008 | Adcox .................... | G16H 30/40 606/130 |
| 2008/0208912 A1 | 8/2008 | Garibaldi | |
| 2008/0287909 A1 | 11/2008 | Viswanathan et al. | |
| 2008/0294232 A1 | 11/2008 | Viswanathan | |
| 2009/0082722 A1 | 3/2009 | Munger et al. | |
| 2009/0105579 A1 | 4/2009 | Garibaldi | |
| 2009/0131955 A1 | 5/2009 | Wenderow et al. | |
| 2009/0245600 A1 * | 10/2009 | Hoffman ................ | A61B 34/30 348/240.99 |
| 2010/0097315 A1 | 4/2010 | Garibaldi et al. | |
| 2011/0144658 A1 | 6/2011 | Wenderow et al. | |
| 2013/0110900 A1 | 5/2013 | Des Jardins et al. | |
| 2013/0345718 A1 * | 12/2013 | Crawford ........... | A61B 17/8866 606/130 |
| 2014/0018792 A1 * | 1/2014 | Gang ................. | A61B 18/1492 606/41 |
| 2014/0068513 A1 | 3/2014 | Sakagawa | |
| 2016/0048636 A1 | 2/2016 | Warner et al. | |
| 2017/0027651 A1 | 2/2017 | Esterberg | |
| 2018/0147721 A1 * | 5/2018 | Griffin ..................... | B25J 9/161 |
| 2018/0173740 A1 * | 6/2018 | Karra ..................... | H04L 67/12 |
| 2018/0218048 A1 * | 8/2018 | Chandramouli .. | G06F 16/24568 |
| 2018/0250086 A1 * | 9/2018 | Grubbs .................. | A61B 34/35 |
| 2018/0275638 A1 * | 9/2018 | Wang .................. | G05B 19/414 |
| 2018/0325610 A1 * | 11/2018 | Cameron ............. | A61B 5/1072 |
| 2018/0338806 A1 * | 11/2018 | Grubbs .................. | A61B 34/30 |
| 2019/0029765 A1 * | 1/2019 | Crawford ............. | A61B 90/361 |
| 2019/0250859 A1 * | 8/2019 | Greene ................. | G06F 3/0685 |
| 2020/0352657 A1 * | 11/2020 | Fanson .................. | A61B 34/20 |
| 2023/0285091 A1 * | 9/2023 | Crawford ............ | B25J 15/0491 606/1 |

\* cited by examiner

PLATFORM FOR FACILITATING REMOTE ROBOTIC MEDICAL PROCEDURES

CROSS-REFERENCE TO RELATED APPLICATION

This non-provisional patent application claims priority under 35 U.S.C. § 119(e) to U.S. Provisional Patent application, Ser. No. 62/819,716, filed Mar. 18, 2019; U.S. Provisional Patent application, Ser. No. 62/932,018, filed Nov. 7, 2019; and U.S. Provisional Patent application, Ser. No. 62/991,010, filed Mar. 17, 2020, the disclosure of which are incorporated by reference.

FIELD

This application relates in general to robotic medical apparatuses and, in particular, to a platform for facilitating remote robotic medical procedures.

BACKGROUND

Modern surgery typically involves one or more attending surgeons operating on a patient within a sterile surgical suite with the assistance of a staff of nurses and healthcare professionals. The patient is ordinarily positioned on a surgical table centered within the surgical suite with booms typically containing lighting and electronic medical provisioning equipment, such as electrocardiographic monitors and visualization displays for visual and non-visual imaging modalities, extending down from the ceiling. Even in a well-equipped surgical suite, the numbers of personnel and amount of support equipment can make modern surgery a logically challenging endeavor.

In response, surgical robotic systems have been developed that allow surgeons and staff to work at a distance from the patient through surgical robotic systems that can remotely manipulate surgical instruments, such as a catheter or stent insertion tool, through robotic actuation. Many conventional surgical robotic systems employ a physically-tethered remote controller that physically limits the operating distance of the surgeon from the patient.

Some surgical robotic systems allow the operating distance to be considerably increased by adding a control and visualization setup that relies on transmitting information, including information about the operative field around the patient and commands from the surgeon's movements via the remote controller to the surgical robot, across a form of data communications network or relay, such as a single dedicated broadband channel, often analog but sometimes digital, albeit at significant cost in terms of infrastructure and expense. Typically, bandwidth is strictly limited and only a small proportion of the visualization and control information can be made available in real- or near-real-time.

The costs of surgical robotic systems can be prohibitive and present an impediment to access to care. As of this time, only about ten percent of hospitals in the United States are equipped with surgical angiography suites due to the costs of the dedicated resources required to provide control and visualization information efficiently at a distance and due to the cost of the duplication of equipment that must be present both within the angiography suite, where the patient is sited, and the remote site within which the surgeon operates.

Some forms of invasive surgery, such as cardiac ablation and interventional radiology, require an angiography suite within which imaging tools, such as bi-plane fluoroscopy, echocardiography, angiography, and noncontact mapping, are in continuous or near-continuous use to respectively ensure proper guidance and placement of an ablation catheter within the atria of the heart or a stent within a vein or artery. Although such imaging tools help eliminate unintended consequences, such as transseptal, transveinal, or transarterial perforation and ensure against occlusion of the pulmonary veins, the surgeon and support staff are unavoidably exposed to radiation from the imaging tools which, over time, can be of grave concern to their long-term well-being, even when stationed outside of the angiography suite and where proper radiation protective gear is used.

Conventional visual imaging modalities that facilitate remote robotic operations, whether analog or digital, provide a video-based user interface of the operative field, including through the use of two-dimensional (2D) monitors and three-dimensional (3D) virtual reality wearable goggles or displays. Typically, visual light or X-ray-based video is captured, compressed, and transmitted over a dedicated connection from the patient site to the remote operator site where the surgeon works. The video is decompressed and displayed to the surgeon to provide an interpretable view of the operative field; however, this video-based method of data-transmission is slow and inefficient, which ultimately results in latency delays being reflected in the visualization of the operative field. This conventional approach to capturing operative field information and remote-site video conversion can result in substantial and compromising loss of information, including crucial raw 3D positional information of in situ surgical instruments that can negatively impact surgical performance and outcome, particularly if a latency delay occurs at a critical stage, such as catheter placement and application of RF energy onto the wall of the heart or stent placement and expansion.

Therefore, a need remains for a reliable, low-latency, highly-scalable, and high efficiency remote-robotic information and control communication, coordination, and transfer apparatus for use in surgical robotic systems.

SUMMARY

A hardware platform includes one or more adapters to interface with medical provisioning equipment involved in a remote robotic medical procedure at a patient site and a software system component, potentially cloud-based, running specialized software to process real-time incoming data streams originating from the medical provisioning equipment and a database to store the data streams for later use or archival. Each data stream can itself contain one or more different types of sensory data as provided through sensors or monitors co-located at the patient site. The software system component provides overall control and overrideable supervision over the remote robotic operations includes a state manager that synergistically processes the incoming data streams, which may be of varying transmission rates, times of receipt or transmission, resolution, and quality. The state manager forms a near-real-time or real-time virtual representation (hereon forward, simply "RTVR") of the operative field. The software system component also includes a data broker that is able to parse the RTVR into subsets of the data tailored to the needs of the medical provisioning equipment and medical monitoring equipment, which may also be deployed and co-located at the patient site.

One embodiment provides a platform for facilitating remote robotic medical procedures. At least one incoming data stream including sensory data is obtained from medical provisioning equipment involved in a remote robotic medical procedure at a patient site. The at least one incoming data stream includes one or more different types of sensory data. At least one computer including a processor is coupled to a memory storing computer-executable code. The processor is configured to receive the at least one incoming data stream into a state manager that is adapted to synchronize and derive from the one or more different types of sensory data a near-real-time virtual representation of an operative field at the patient site. The processor is further configured to provide the near-real-time virtual representation to a data broker that is adapted to parse the near-real-time virtual representation into one or more subsets adapted to needs of requesting component.

Still other embodiments and applications will become readily apparent to those skilled in the art from the following detailed description, wherein are described embodiments by way of illustrating the best mode contemplated. As will be realized, other and different embodiments are possible and their several details are capable of modifications in various obvious respects, all without departing from the spirit and the scope. Accordingly, the drawings and detailed description are to be regarded as illustrative in nature and not as restrictive.

DETAILED DESCRIPTION

The disclosures of U.S. Provisional Patent application, Ser. No. 62/819,716, filed Mar. 18, 2019, and U.S. Provisional Patent application, Ser. No. 62/932,018, filed Nov. 7, 2019, are incorporated herein by reference as if set forth in full for all purposes.

General Background

In part in response to concerns over undue exposure to radiation by surgical staff, as well as the need to increase access to care to locations that are not equipped with the same degree of surgical capabilities, surgical robotic systems have been developed that allow surgeons and their supporting staff to work outside of the radiation field caused by some types of visual and non-visual imaging modalities as used in procedures requiring real-time or near real-time representation of the operative field of the patient.

Figure 1:
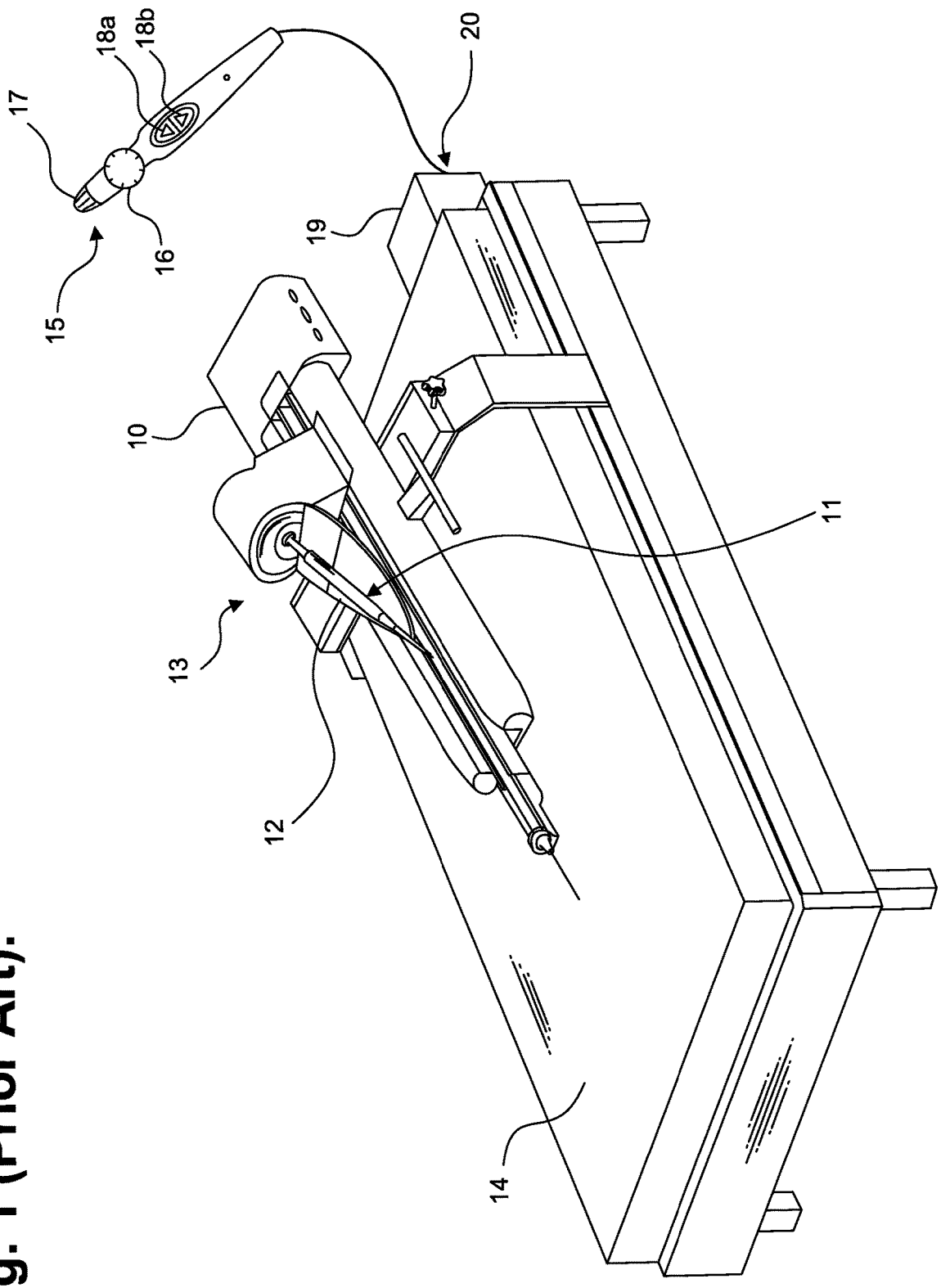
FIG. 1 is a prospective view showing a prior art remotely-controllable medical robotic operating suite.

For instance, in the field of cardiac catheter ablation, surgical robotic systems have been developed to remotely manipulate an ablation catheter through robotic actuation. Surgical robotic systems also exist for use in other fields of medicine and surgical endeavor. FIG. 1 is a prospective view showing a prior art remotely-controllable medical robotic operating suite 9. One such surgical robotic system 13, the Amigo Robotic Catheter System from Catheter Robotics, Mount Olive, NJ, provides a robotic arm 10 on a rollable gantry 12 that straddles a surgical table 14 on a pair of longitudinal tracks or similar structure. Other forms of surgical robotic systems for cardiac ablation and similar surgical procedures and other forms of robotic medical surgical methodologies both exist.

Preliminary to beginning a robotic cardiac ablation procedure, a remote ablation catheter controller 12 is positioned within the robotic arm 10 and the ablation catheter 22 is guided into the patient's heart through manual surgical procedure. The robotic arm 10 can be remotely controlled by the surgeon using a wired remote controller 15 that allows catheter rotation 17, tip deflection 16, and control over insertion 18a and withdrawal 18b of the catheter 22.

Other forms of non-radiation emitting imaging modalities exist. For example, the specific Amigo Robotic Catheter System surgical robotic system 13 works in combination with the CARTO-3 3D mapping system from Biosense Webster, Irvine, CA, and uses a set of three electromagnetic fields to visualize the thoracic region of a patient at an approximate 50 Hz sampling frequency in near-real-time. Other types and forms of visual and non-visual imaging modalities exist using, for instance, impedance or location-based sensors.

The tip of the catheter 22 has an electromagnet and through triangulation with the other electromagnets, the catheter's position within the heart is tracked and a 3D rendering is created, although display generated through triangulation is limited to the confines of a 2D display. Contact force is measured at the catheter tip (not shown) to provide feedback of catheter-tissue contact. Cardiac ablation is performed by creating point-by-point lesions around the left and right pulmonary vein ostia. Conduction block is confirmed by recording the pulmonary vein potentials on the circular mapping catheter and by pacing maneuvers.

The remote controller 15 is physically tethered to the robotic system 13 and the length of the cord connecting the remote controller 15 to the robotic system 13 physically limits the operating distance of the surgeon from the patient. However, similar forms of surgical robotic systems exist in which the operating distance between surgeon and patient can be increased by transmitting surgical information across a network, typically a dedicated (and expensive) analog or digital broadband network, including both information about the operative field and commands from the surgeon's movements of the remote controller to the surgical robot. This type of setup is limited to operate only point-to-point, that is, between a specific angiography (or surgical) suite and a specific remote control suite sharing a dedicated hardwired connection. The patient receives medical (surgical) care in the within the angiography (or surgical) suite and the surgeon remotely performs an operation on the patient from within the angiography suite.

Platform Infrastructure

In accordance with one embodiment, a hardware platform includes one or more adapters to interface with medical provisioning equipment involved in a remote robotic medical procedure at a patient site. The hardware platform further includes a software system component, potentially cloud-based, running specialized software to process real-time incoming data streams originating from the medical provisioning equipment.

Figure 2:
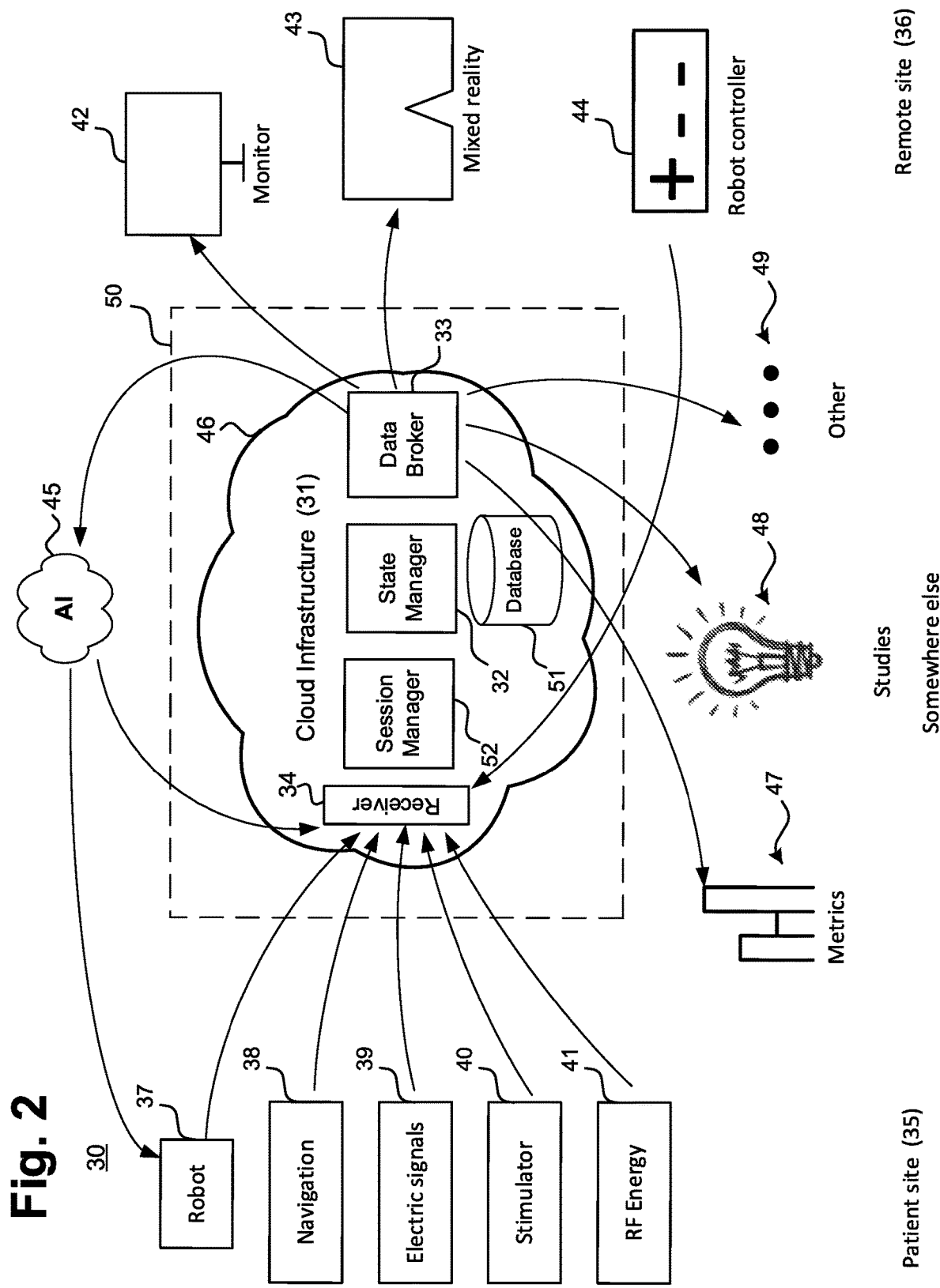
FIG. 2 is a block diagram showing, by way of example, a platform for facilitating remote robotic medical procedures in accordance with one embodiment.

In a further embodiment, the hardware platform includes one or more to process real-time outgoing data streams originating from the medical monitoring equipment. FIG. 2 is a block diagram showing, by way of example, a platform 30 for facilitating remote robotic medical procedures in accordance with one embodiment. The medical provisioning equipment refers to medical devices and sensors, which may be individual devices or sensors, or equipment that combines both. Such equipment is typically deployed within the surgical suite at the patient site 35 to typically detect and quantify voltage, pressure, sound, chemical presence, light reflectance, light absorption, electromagnetic energy, radiofrequency energy, infrared energy, and other physical and physiological measurables.

The location and orientation of the sensors and devices within the patient (target) site is often of paramount importance, particularly when the operating staff is located at a remote site. In some cases, the medical provisioning equipment generates coordinates describing one or more of the position and orientation of the medical provisioning equipment within the patient site 35. The medical provisioning equipment can include, by way of example, a surgical robotic system 37, such as the Amigo Robotic Catheter System, a navigational system 38, such as the CARTO-3 3D mapping system, electrical signal generators 39, stimulators 40, and sources of radio frequency (RF) 41 or other energies, such as used to effect cardiac ablation. The medical provisioning equipment can include any combination of sensors and devices capable of detecting and quantifying voltage, pressure, sound, chemical presence, light reflectance, light absorption, electromagnetic energy, radiofrequency energy, and infrared energy The medical monitoring equipment generally refers to medical devices and sensors that are deployed within the remote site 36 where the surgeon and his staff work remotely from outside the angiography (surgical) suite and can include, by way of example, one or more 2D monitors 42, mixed or "virtual" reality visualization goggles or headgear 43, a robotic controller 44, such as the wired remote controller 15 (shown in FIG. 1), or for other purposes, such as datan analytics and metrics 47, retrospective studies 48, and so forth 49. In some cases, however, medical monitoring equipment, such as a display device, may also be present at the patient site 35. Similarly, in some cases, medical provisioning equipment, such as a remotely controllable robotic device involved in the remote robotic procedure, maybe also be present at the remote site 36. Other types and forms of medical provisioning and monitoring equipment exist. In yet a further embodiment, the medical monitoring equipment can be set up to visualize and provide a representation of the operative field at the patient site 35 via at least one outgoing data stream.

The software system component 50 can be implemented on a standalone server or suite of servers (not shown), or could be implemented through a cloud infrastructure 31, such as provided by companies, such as Amazon, Seattle, WA, through their Amazon Web Services cloud services offerings. Many other companies offer cloud services of various types and capabilities. For purposes of illustration, and without inferring limitations of any sort, the software system component 50 will be described herein as operating through a cloud infrastructure 31 that provides cloud services over a wide area digital (and possibly also analog) data communications network, such as the Internet 46.

Cloud services, generally provided over the Internet 46, are becoming increasingly popular because they provide on-demand availability of physical computer system resources that are oftentimes further offered with a guarantee of continuous availability or up-time, so service continuity is assured, a characteristic of crucial importance in the field of remote robotic surgery. Cloud services are an attractive and cost-effective alternative to traditional in-house computer system setups or server farms, particularly as readily-scalable data storage and computing power remain on tap without requiring end-user purchasing of additional dedicated server hardware and networking resources (other than locally-situated computing resources as needed to utilize the cloud services). Moreover, direct active management by the user is not required.

The software system component 50 contains at least three modules, a session manager 52, a state manager 32 and a data broker 33. The software system component 50 includes a database 51 to store data streams, both incoming and outgoing, and RVTR, for later use or archival, preferably in a manner compliant with HIPPA, European and other patient privacy regulations.

The forms of the incoming and outgoing data streams depends upon the communications utilized. For instance, the Internet employs the Internet protocol suite, known as TCP/IP (Transmission Control Protocol/Internet Protocol), which is implemented through a combination of end-to-end and point-to-point connections. The Internet is a digital data communications network that has connections worldwide and information is conveyed over the Internet through messages. Other forms of data communications networks, whether publically available or private, digital, analog, or hybrid, and so on, exist.

Receiver

In addition, the software system component 50 can contain a receiver module 34. Incoming streams of data are received initially by at least one receiver module 34 that provides a common Web-enabled interface for the medical monitoring devices deployed at the patient site 35. Although shown with reference to FIG. 1 as appearing within the cloud infrastructure 46, the receiver module 34 could alternatively be deployed locally at the patient site 35 (and in the further embodiment, at the remote site 36), be contained within the cloud infrastructure 46, located in each of those places, or even be distributed at other locations. Similarly, the software system component 50 can contain a transmitter module (not shown) to direct one or more outgoing streams of data that in turn can contain one or more different types of data.

Figure 3:
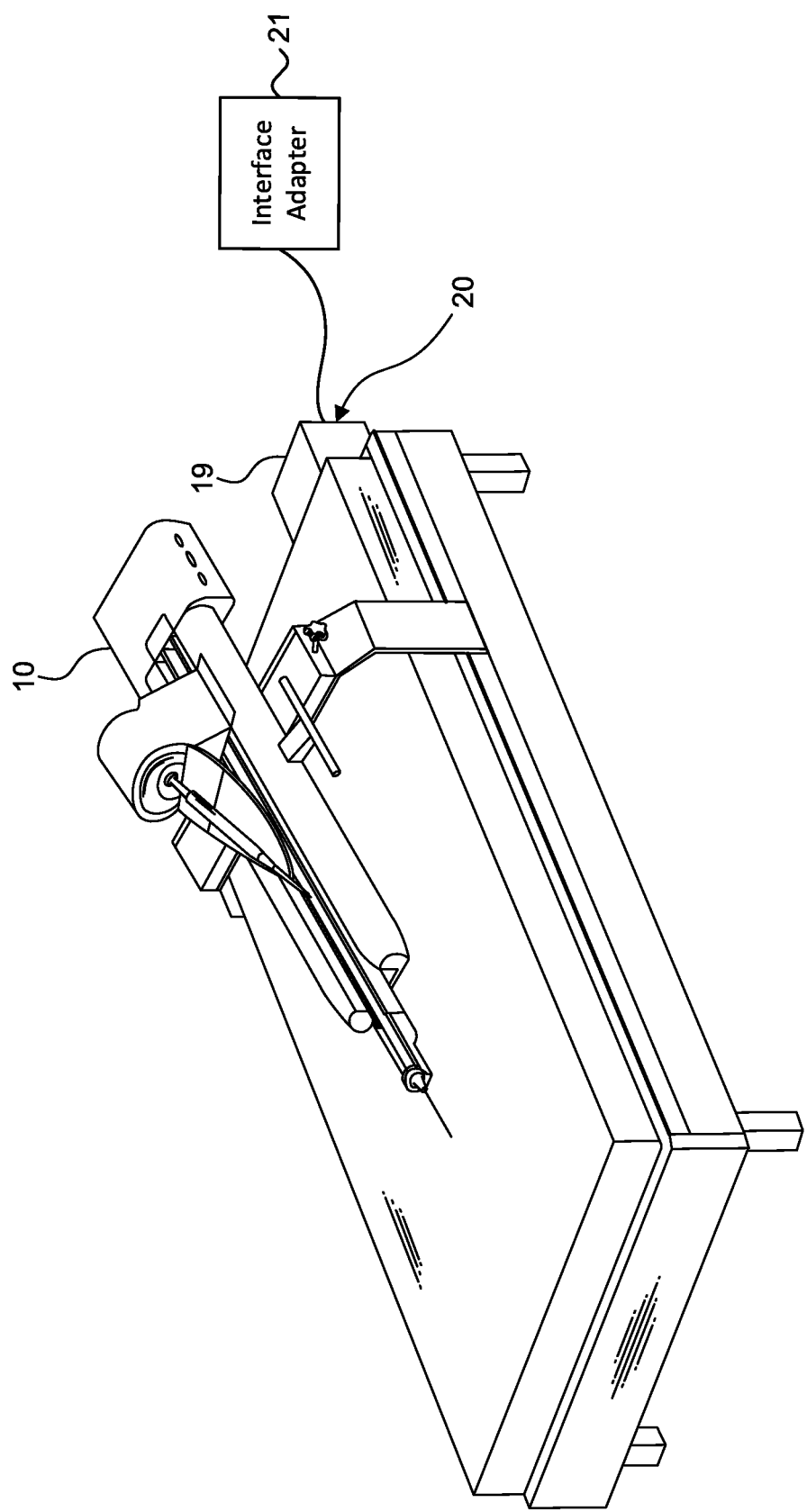
FIG. 3 is a side view showing, by way of example, a patient site interface adapter for use with a prior art remotely-controllable medical robotic operating suite.
Figure 4:
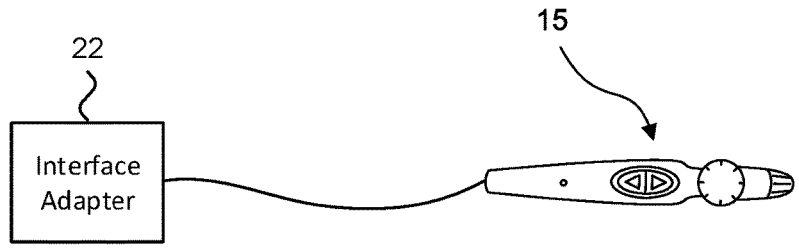
FIG. 4 is a side view showing, by way of example, a remote site interface adapter for use with a prior art remote controller.

The receiver module 34 serves as an adapter that interfaces the various types of medical provisioning equipment at the patient site 35 (and the various types of medical monitoring equipment at the remote site 36) with the software system component 50. The receiver module 34 can be conceptually seen as a single component, although in practice, separate components may be required for the patient site 35 and the remote site 36, for instance, to effect a remote wireless connection over the Internet. FIG. 3 is a side view showing, by way of example, a patient site interface adapter 21 for use with a prior art remotely-controllable medical robotic operating suite. FIG. 4 is a side view showing, by way of example, a remote site interface adapter 22 for use with a prior art remote controller. The adapters can be coupled to the medical provisioning equipment or the medical monitoring equipment and can include, by way of example, a digital-to-analog converter (DAC), digital signal filter, analog signal filter, signal amplifier, and signal attenuator. Still other forms and types of adapters are possible.

The patient site interface adapter 21 plugs into a control panel 20 as part of a control interface 19 on the surgical robotic system 13. In the particular example described supra, the Amigo Robotic Catheter System uses an I2C electrical serial bus interface that is ordinarily used to connect the wired remote controller 15. In a prototype setup, an I2C interface compatible connector is mated to a Raspberry Pi single board computer, offered through the Raspberry Pi Foundation in the United Kingdom and manufactured in various countries, through the Raspberry Pi's general purpose input-output (GPIO) connector. The local Raspberry Pi operates under a version of the Raspian operating system, which allows the computer to remotely interface to another nearby Raspberry Pi using a built-in Wi-Fi interface. In a further embodiment, the local Raspberry Pi can interface to a distant Raspberry Pi over the Internet. In either situation, whether interfacing with a nearby or distant Raspberry Pi, the wired remote controller 15 is itself interfaced through a similar I2C interface, thereby allowing the wired remote controller 15 to be operated remotely from the physical locality of the surgical robotic system 13. Other types of interfacing and adapter setups are possible, including interfaces specifically intended to allow proprietary medical provisioning equipment to communicate to the software system component 50.

Session Manager

The session manager 52 ensures that both the incoming and outgoing data streams remain associated with their originating session. Particularly when implemented through a cloud infrastructure 31, the medical provisioning equipment at different patient sites 35 and the medical monitoring equipment at different remote sites 36 could be simultaneously interfacing to the receiver 34 and therefore the different aspects of the software system component 50, including the state manager 32 and the data broker 33. The session manager 52 keeps the associations of the incoming and outgoing data streams with their originating medical provisioning and monitoring equipment straight.

State Manager

A single medical monitoring device could generate one or more incoming data streams. In turn, each incoming data stream can contain one or more types of sensory data. A problem occurs within the software system component 50 due to the disparate rates of receipt, varying quality of data received due to transmission limitations and errors, and the different types of sensory data that could be received from a single device, including visual data in digital or analog form, or potentially in both digital and analog form, textual or human-readable codes, or binary- or machine-encoded information.

The state manager 32 reconciles these incoming data stream data type considerations. The state manager 32 synchronizes, if necessary, pieces of sensory data that may arrive out of temporal order or sequence based on time stamps or some other form of temporal or serializational marker added to the data prior to transmission, and derives an RTVR by evaluating the sensory data and building a virtual representation based upon the contributions made by each of the incoming data streams and data types. The state manager 32 can include an aggregation module (not shown) that evaluates and assembles the different types of sensory data into the RTVR, or possibly into other types of data representations, all of which can also be potentially forwarded through an outgoing data stream to the medical provisioning equipment at the patient site 35 and the medical monitoring equipment at the remote site 36, stored in the database 51, or both. For example, the aggregation module can aggregate position, rotation, and orientation data from the different types of sensory data into a representation of the patient site 35. In a still further embodiment, the aggregation module can aggregate the sensory data from a sensor, device, or both into the RTVR to represent position and rotation of the sensor, device, or both within the patient site 35, which can be invaluable to the operating surgeon.

In a further embodiment, the software system component 50 includes a heuristics module (not shown), which is embedded through executable computer code in artificial intelligence (AI) 45, that can generate autonomous control functions for the medical monitoring equipment at the remote site 36. The data broker 33 forwards the autonomous control functions via the transmitter (not shown) in at least one outgoing data stream. For instance, a command might originate from a wired remote controller 15 that is connected to a remote site interface adapter 22 before intended and the heuristics module will intercept and, if appropriate and with the proper medical protocol safety precautions, override or cancel the command originally sent from the wired remote controller 15.

In a yet further embodiment, the software system component 50 includes a heuristics module (not shown), which is embedded through executable computer code in artificial intelligence (AI) 45, that can determine one or more of a previous, a present, and a predicted future state of the medical procedure underway and to integrate the previous, present, or predicted future state into the RTVR or other output format.

In a still further embodiment, the software system component 50 includes an analysis module (not shown), which is embedded through executable computer code in artificial intelligence (AI) 45, that algorithmically evaluate one or more subsets of the RTVR to arrive at an analytical result.

Data Broker

The state manager 32 works closely with the data broker 33 to maintain and make available an RTVR to the medical provisioning equipment at the patient site 35 and the medical monitoring equipment at the remote site 36. The medical provisioning equipment and medical monitoring equipment includes components, including devices and sensors of varying capabilities. The data broker 33 adapts the RTVR to each equipment's specific data needs by parsing the near-real time virtual representation into one or more subsets adapted to needs of the requesting component.

Control Flow

Figure 5:
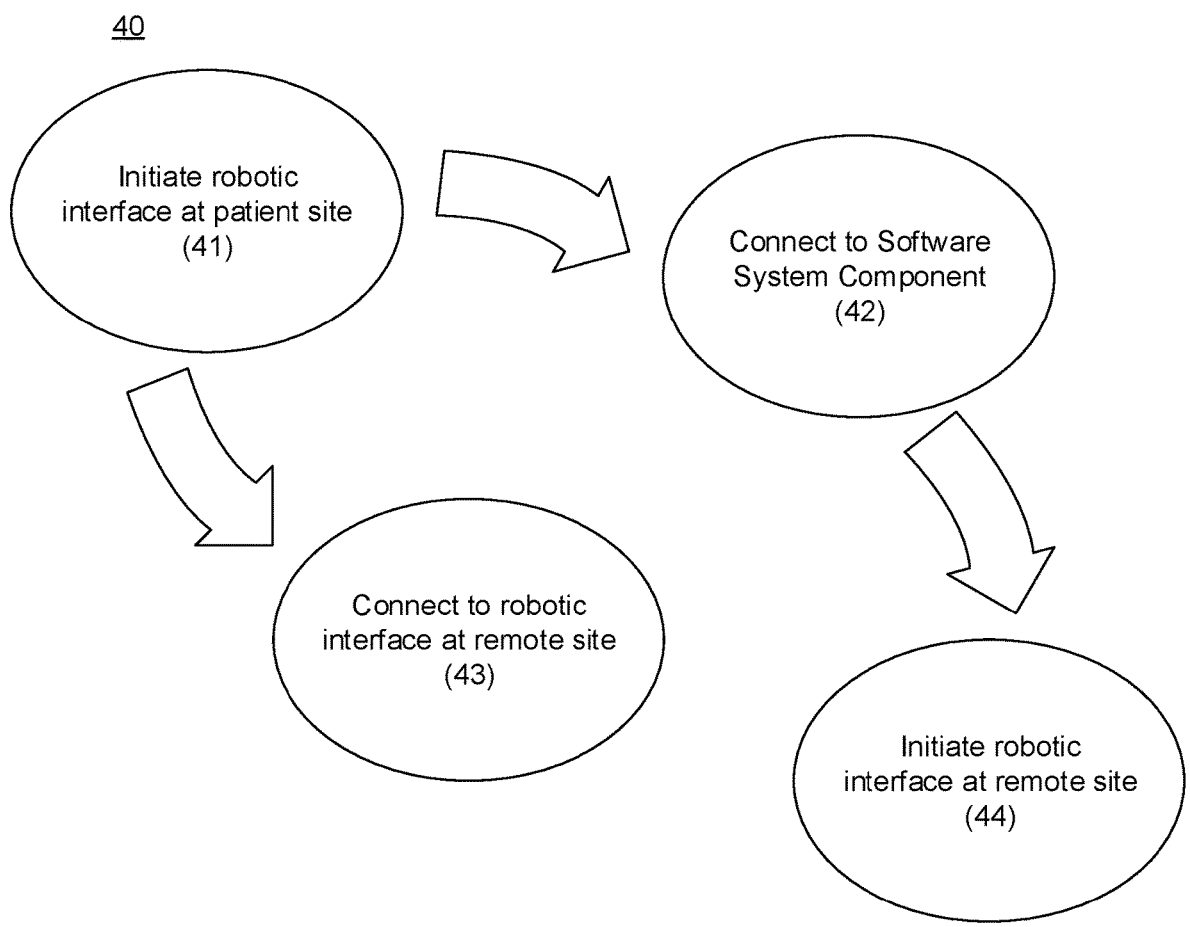
FIG. 5 is a process flow diagram showing initialization of the platform of FIG. 2.

Operationally, the platform 30 is typically setup through a step-by-step series of connections, wired, wireless, or a combination of both. FIG. 5 is a process flow diagram showing initialization 60 of the platform 30 of FIG. 2. The process generally begins by initiating a robotic interface at the interface adapter 21 at the patient site 35 (step 61). Initiation involves the interface adapter 21 making electrical communicative contact with the surgical robotic system 37 though the control panel 20 in lieu of the wired remote controller 15. The interface adapter 21 then connects to both the software system component 50 (step 62) and, in some situations, directly to the interface adapter 22 at the remote site 36 (step 63). The software system component 50 also connects to the interface adapter 22 at the remote site 36 into which the wired remote controller 15 is connected (step 64), which completes the process of initialization 60.

Process Flow

Figure 6A:
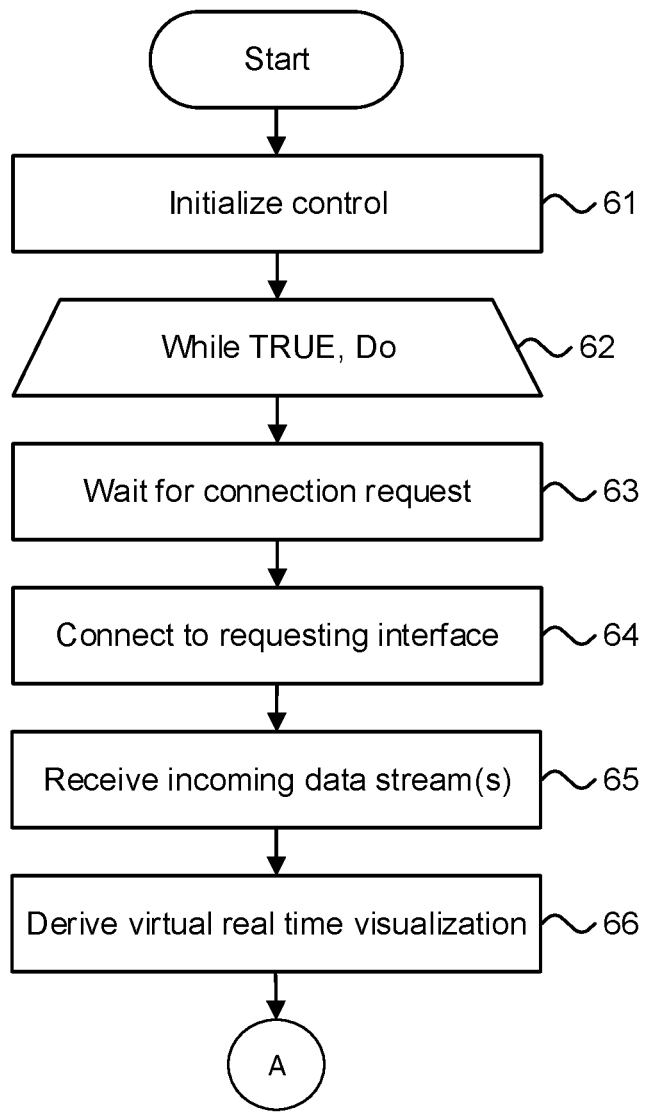
FIGS. 6A-6B is a flow diagram showing facilitating remote robotic medical procedures through use of the platform of FIG. 2.
Figure 6B:
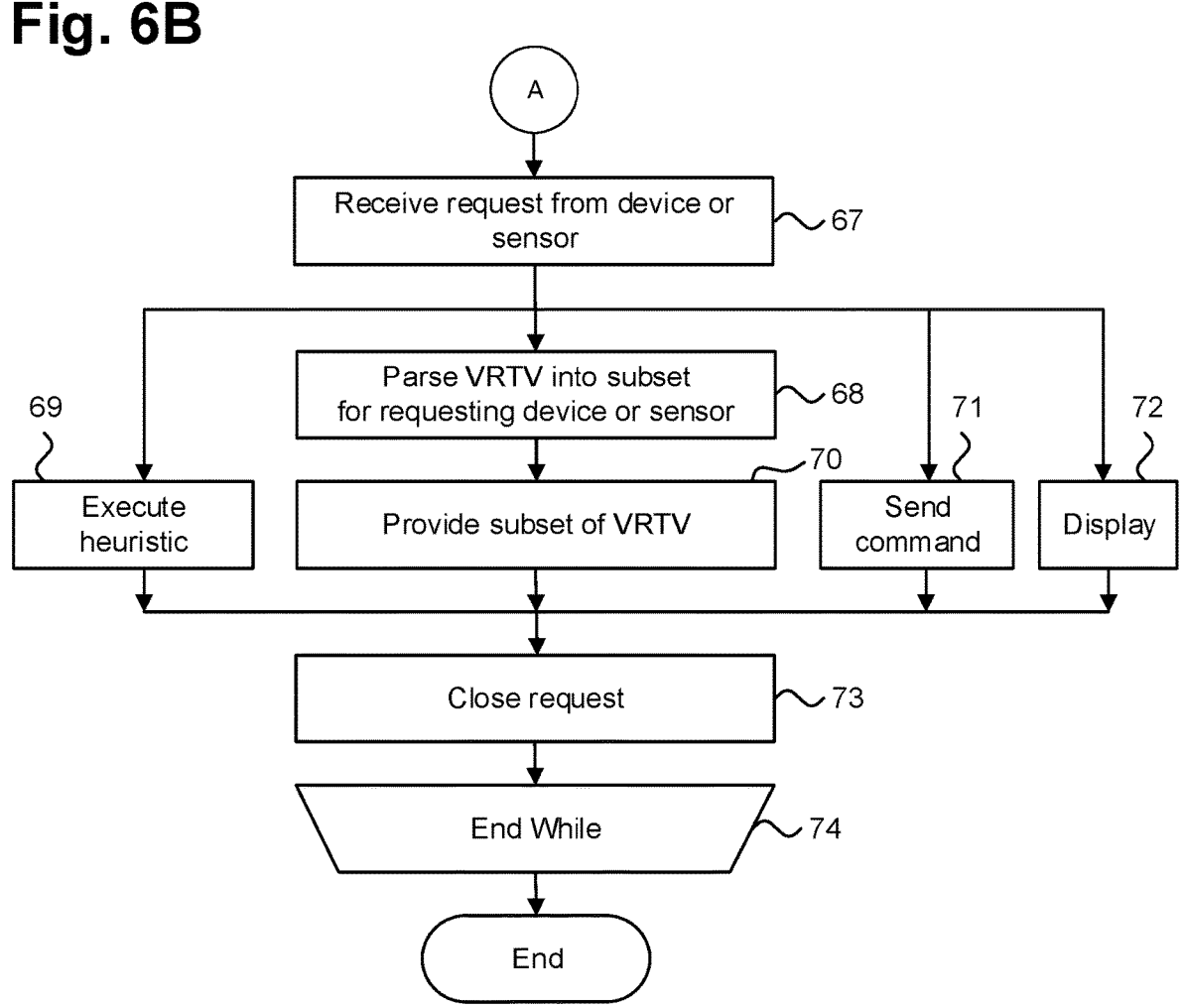

The software system component 50, whether implemented on a standalone server or through a cloud infrastructure 31, iteratively performs a routine of steps that coordinate the actions of the various sensors, devices, and actors at the various sites. FIGS. 6A-6B is a flow diagram showing facilitating remote robotic medical procedures 60 through use of the platform 30 of FIG. 2. First, the control is initialized (step 61), as described in detail supra with reference to FIG. 5. An iterative control loop (steps 62-83) is then repeatedly executed. During each iteration, the software system component 50 waits for a connection request from an interface adapter 21 at a patient site 35 (step 62), then makes the connection upon receive the connection request (step 63).

As the remote robotic procedure proceeds, one or more incoming data stream is received (step 65) and the session manager 52 ensures that both the incoming and outgoing data streams remain associated with their originating session. The state manager 32 synchronizes and derives an RTVR of an operative field at the patient site 35 from the different types of sensory data included in the incoming data streams (step 66). The software system component 50 also receives requests from devices or sensors that are part of the medical provisioning or monitoring equipment (step 67) and, depending upon the type of requestor, different actions may take place. For instance, the heuristics module (not shown) may execute a heuristic (step 69), the broker 33 may forward an autonomous control function or command (step 71), or all or part of the RTVR may be displayed (step 72). As well, the requestor might only require a subset of the RTVR, which the data broker 33 will need to parse (step 58) and then provide to the requestor (step 70).

One or more of the foregoing action in response to a request received from devices or sensors that are part of the medical provisioning or monitoring equipment may occur, after which the request is ordinarily considered closed (step 73). The iterative loop repeats (step 74) until the software system component 50 is shut down at some point.

Scaleability

Currently, virtual machines have become readily deployable, particularly through a cloud infrastructure 31. Various forms of container orchestration systems are available, including Kubernetes and Docker. These systems allow virtual machine and operating environments to be quickly prototyped and fielded without regard to particular underlying hardware idiosyncrasies. Here, one or more instances of the software system component 50 can be deployed, vastly opening up access to care by allowing control over multiple instances of surgical robotic systems from a single control point, particularly when implemented in the cloud.

While the invention has been particularly shown and described as referenced to the embodiments thereof, those skilled in the art will understand that the foregoing and other changes in form and detail may be made therein without departing from the spirit and scope.

The invention claimed is:

1. A platform for facilitating remote robotic procedures, comprising:
   a plurality of incoming data streams comprising sensory data obtained from provisioning equipment involved in a remote robotic procedure at a target site, the plurality of incoming data streams comprising different types of sensory data, wherein the sensory data comprises sensory data pieces associated with markers; and
   at least one computer comprising a processor coupled to a memory storing computer-executable code, the processor configured to:
      receive incoming data streams into a state manager, wherein at least some of the data streams are received at disparate rates from each other and at least some of the sensory data in the received data streams is received out of temporal sequence, the state manager adapted to synchronize the incoming data streams at least partially based on the markers associated with the sensory data pieces and derive from the different types of sensory data a near-real time virtual representation of an operative field at the target site;
      provide the near-real time virtual representation to a data broker that is adapted to parse the near-real time virtual representation into one or more subsets adapted to needs of a requesting component;
      a heuristics module adapted to generate using artificial intelligence at least one autonomous control function comprising determining a correct time for a user command, detecting the user command prior to the correct time, and generating the autonomous control function to override the user command based on the detection; and
      an at least one outgoing data stream further comprising the at least one autonomous control function directed to the provisioning equipment.

2. A platform in accordance with claim 1, the state manager further comprising:
   an aggregation module adapted to aggregate the different types of sensory data into the near-real time virtual representation.

3. A platform in accordance with claim 1, the state manager further comprising:
   an aggregation module adapted to aggregate one or more of position, rotation, orientation data from the different types of sensory data into at least one of an representation of a remote target site.

4. A platform in accordance with claim 1, further comprising:
   the provisioning equipment comprising one of a sensor and a device adapted to detect and quantify one or more of voltage, pressure, sound, chemical presence, light reflectance, light absorption, electromagnetic energy, radiofrequency energy, and infrared energy.

5. A platform in accordance with claim 4, the state manager further comprising:
   an aggregation module adapted to aggregate the sensory data from the one of a sensor and a device into the near-real time virtual representation to represent position and rotation of the one of a sensor and a device within the target site.

6. A platform in accordance with claim 4, the state manager further comprising:
   the provisioning equipment further comprising a plurality of the one of a sensor and a device; and
   an aggregation module adapted to aggregate the sensory data from the plurality of the one of a sensor and a device into the near-real time virtual representation to represent location and orientation of the plurality of the one of a sensor and a device within the target site.

7. A platform in accordance with claim 6, wherein the one of a sensor and a device is adapted to visualize and provide a representation of an operative field at the target site into at least one of the outgoing data streams.

8. A platform in accordance with claim 1, the state manager further comprising:
   a heuristics module adapted to determine a predicted future state of the procedure and to integrate the predicted future state into the near-real time virtual representation.

9. A platform in accordance with claim 1, each incoming data stream further comprising:
   an analog data feed transmitted by the provisioning equipment; and
   a digital data feed derived from the provisioning equipment.

10. A platform in accordance with claim 9, further comprising:
an adapter operatively coupled to the provisioning equipment and comprising at least one of:
a digital-to-analog converter;
a digital signal filter;
an analog signal filter;
a signal amplifier; and
a signal attenuator.

11. A platform in accordance with claim 1, further comprising:
the provisioning equipment adapted to generate coordinates further comprised in the at least one of the incoming data streams describing one or more of position and orientation of the provisioning equipment within the target site.

12. A platform in accordance with claim 1, wherein the at least one incoming data stream comprises one or more messages.

13. A platform in accordance with claim 1, the requesting component comprising:
a display device involved in the remote robotic procedure at a remote site.

14. A platform in accordance with claim 1, the requesting component comprising:
remotely controllable provisioning equipment involved in the remote robotic procedure at a remote site.

15. A platform in accordance with claim 1, the requesting component comprising:
an analysis module adapted to algorithmically evaluate the one or more subsets of the near-real time virtual representation to arrive at an analytical result.

16. A platform in accordance with claim 1, wherein the at least one computer is comprised within an online cloud computing center.

17. A platform in accordance with claim 1, wherein the markers are one of temporal markers and serialization markers.

18. A platform in accordance with claim 1, wherein the sensory data does not comprise sound data.

19. A platform in accordance with claim 1, wherein at least some of the incoming data streams comprise human-readable codes and the state manager is further adapted to derive the near-real time virtual representation of the operative field at the target site using the human-readable codes.

* * * * *